(12) United States Patent
Redlingshoefer et al.

(10) Patent No.: US 7,582,800 B2
(45) Date of Patent: *Sep. 1, 2009

(54) PROCESS FOR PREPARING ALKYL MERCAPTANS IN A MULTIZONE FIXED BED REACTOR

(75) Inventors: Hubert Redlingshoefer, Münchsteinach (DE); Christoph Weckbecker, Gründau-Lleblos (DE)

(73) Assignee: Degussa GmbH, Dusseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/827,154

(22) Filed: Jul. 11, 2007

(65) Prior Publication Data

US 2008/0015390 A1 Jan. 17, 2008

(30) Foreign Application Priority Data

Jul. 13, 2006 (DE) .................. 10 2006 032 635

(51) Int. Cl.
*C07C 319/00* (2006.01)

(52) U.S. Cl. ......................................... 568/61; 568/71

(58) Field of Classification Search .................. 568/61, 568/71
See application file for complete search history.

(56) References Cited

U.S. PATENT DOCUMENTS 3,053,902 A * 9/1962 Doumani .................... 568/71
5,847,223 A * 12/1998 Ponceblanc et al. ........... 568/71
5,886,230 A * 3/1999 Hofen et al. .................. 568/71
2005/0080295 A1 4/2005 Redlingshofer et al.
2006/0135816 A1 6/2006 Redlingshofer

FOREIGN PATENT DOCUMENTS

| EP | 0 068 193 A1 | 1/1983 |
|---|---|---|
| EP | 0 832 687 A2 | 4/1998 |
| EP | 0 832 687 B1 | 10/2001 |
| WO | WO 2004/096760 A1 | 11/2004 |
| WO | WO 2005/021491 | 3/2005 |
| WO | WO 2005/021491 A1 | 3/2005 |
| WO | WO 2006/015668 A1 | 2/2006 |
| WO | WO 2006/063669 | 6/2006 |
| WO | WO 2006/063669 A1 | 6/2006 |

OTHER PUBLICATIONS

Mashkina et al., Catalytic Reactions of n-Propanol and n-Butanol with Hydrogen Sulfide, Kinetics and Catalysis (Translation of Kinetika I Kataliz) (2002), 43(5), 684-690.*

* cited by examiner

*Primary Examiner*—Sikarl A. Witherspoon
*Assistant Examiner*—Chukwuma O Nwaonicha
(74) *Attorney, Agent, or Firm*—Robert G. Weilacher; Smith, Gambrell & Russell, LLP

(57) ABSTRACT

The invention relates to a process for preparing alkyl mercaptans by catalytic gas phase reaction of alkanols and hydrogen sulphide over alkali metal tungstates, the reaction being performed in at least two successive reaction zones which contain catalysts of different activity and selectivity.

17 Claims, No Drawings

PROCESS FOR PREPARING ALKYL MERCAPTANS IN A MULTIZONE FIXED BED REACTOR

CROSS-REFERENCE TO RELATED APPLICATIONS

This application claims the benefit of priority of German Patent Application No. 10 2006 032 635.0 filed Jul. 13, 2006, which is relied on and incorporated herein by reference.

INTRODUCTION AND BACKGROUND

The invention relates to a process for preparing alkyl mercaptans by catalytic gas phase reaction of alkanols and hydrogen sulphide over alkali metal tungstates, the reaction being performed in at least two successive reaction zones which contain catalysts of different activity and selectivity.

Among the alkyl mercaptans, methyl mercaptan in particular is an industrially important intermediate, for example for the synthesis of methionine and for the synthesis of dimethyl sulphoxide and dimethyl sulphone. It is nowadays prepared predominantly from methanol and hydrogen sulphide by reaction over a catalyst composed of aluminium oxide. Methyl mercaptan is synthesized usually in the gas phase at temperatures between 300 and 500° C. and at pressures between 1 and 25 bar.

As well as the methyl mercaptan formed, the reaction mixture comprises the unconverted starting materials and by-products, for example dimethyl sulphide and dimethyl ether, and also gases, for example methane, carbon monoxide, hydrogen and nitrogen. The methyl mercaptan formed is removed from this reaction mixture.

For the economic viability of the process, a very high yield is required in the catalytic reaction of methanol and hydrogen sulphide to give methyl mercaptan, in order to keep the complexity in the removal of the methyl mercaptan formed from the reaction mixture as low as possible. The energy expenditure in particular for the cooling of the reaction mixture to condense the methyl mercaptan constitutes a large cost factor here.

To increase the activity and selectivity, aluminium oxide as a support is typically admixed with potassium tungstate or caesium tungstate. The tungstate is usually used in amounts up to 25% by weight, based on the total weight of the catalyst. An improvement of activity and selectivity is also obtained by increasing the molar ratio of hydrogen sulphide to methanol. Typically, molar ratios between 1 and 10 are employed.

However, a high molar ratio also means a high excess of the hydrogen sulphide in the reaction mixture and hence the necessity of conducing large amounts of gas in circulation. To reduce the energy expenditure required for this purpose, the ratio of hydrogen sulphide to methanol should therefore differ only slightly from 1.

EP 0 832 687 B1 describes the advantages of using caesium tungstate ($Cs_2WO_4$) instead of potassium tungstate ($K_2WO_4$) as a promoter. For instance, use of caesium tungstate allows an enhanced activity with simultaneously good selectivity to be achieved.

Increasing the caesium tungstate concentration to up to 40% by weight allows the selectivity for methyl mercaptan to be enhanced to up to 92% without the activity deteriorating disproportionately.

According to the general view, the best selectivity is achieved with catalysts in which the alkali metal/tungsten ratio is equal to 2:1 (A. V. Mashkina et al., React. Kinet. Catal. Lett., Vol. 36, No. 1, 159-164 (1988)).

These investigations do not take into account that the concentration ratios of reactants and products, but also temperatures in the reactor, differ greatly in the course of the reaction.

It is an object of the present invention to provide a process which features an improved yield over the known processes and hence leads to higher economic viability.

SUMMARY OF THE INVENTION

The invention provides a process for preparing alkyl mercaptans, especially methyl mercaptan, by catalytic gas phase reaction of alkanols, especially methanol, and hydrogen sulphide over a solid alkali metal tungstate, the reactants being converted in at least two successive reaction zones which contain catalysts with activities with respect to mercaptan formation adjusted to the concentration ratios of the reactants in these zones.

This graduation takes account of the fact that the concentration of the reactants decreases during the flow through the reaction zones, while the concentration of the target product simultaneously rises. Moreover, it is taken into account that a considerable excess temperature can be established in the first part of the fixed bed in particular with the highly exothermic reaction present here, since the concentrations of the reactants are at the highest there.

The establishment of reaction zones with different activity also enables the plant load and the space-time yield to be increased, since the incomplete reaction over the less active catalyst in the first zone generates a lower exotherm (maximum excess temperature in the fixed bed) there. The amount of heat released is divided, in accordance with the invention, more uniformly over the reactor. This in turn enables the reactant flow, which is limited by a maximum permissible exotherm, to be raised.

These advantages are based on the inventive measure of using catalysts with different activities, selectivities or else thermal stressability in the different zones. In the second or further subsequent reaction zones, preference is given to using a catalyst with a higher activity for alkyl mercaptan formation than in the first reaction zone, which is suitable for accelerating and for completing the alkyl mercaptan formation even at the lower concentration of the reactants in the second reaction chamber. At the same time, it preferably only insignificantly (selectivity preferably $\leq 1\%$), if at all, catalyses by-product formation from the alkyl mercaptans present there in excess compared to the reactants, for example to give dimethyl sulphide or dimethyl disulphide.

DETAILED DESCRIPTION OF THE INVENTION

In the first reaction zone, in contrast, preference is given to using a catalyst which, in addition to the alkyl mercaptan formation, catalyses the reaction of alkanols and hydrogen sulphide in parallel reactions, for example to give dimethyl ether, only insignificantly (selectivity preferably $\leq 1\%$), if at all. These catalysts are preferably less active with regard to mercaptan formation than the catalysts of the second reaction zone. Moreover, the catalysts for the first reaction zone are preferably more highly thermally stressable and also afford alkyl mercaptan with good selectivity at high temperatures.

Between the reaction zones, there is no feeding of reactants. The activities and selectivities of the catalysts to be used can be determined easily by standard experiments. The reactivity can be reported in mol of mercaptan/($m^3$ of reaction space * h) or % alkanol conversion. The activity of the catalyst is at least 1% higher in the second reaction zone under identical standard experimental conditions than that of the catalyst used in the first reaction zone, especially 10 to 50% higher.

Preference is given to reaction zones in the form of fixed beds which are connected directly to one another. The inventive linkage of reaction zones is independent of the design of the reactor. For instance, it is possible to implement a plurality of reaction zones in all industrial fixed bed reactors. For example, in a vertical tubular reactor, different reaction zones would arise in flow direction through filling of the tube with different catalysts at different heights. The reaction zones can additionally be optimized by different geometries or by separate heating or cooling circuits of heat carrier media.

The length, the diameter and the volume of the individual reaction zones depends upon the activity of the catalysts used.

In the 1st zone, preference is given to using a catalyst with an activity in mercaptan formation which is lower than that of the catalyst used in the following section(s).

In this way, with the present exothermic reaction, very high local overheating is avoided in the 1st section, while the higher activity for mercaptan formation in the second section leads to virtually complete conversion of the reactants yet to be converted. For methanol, a conversion of 99% was measured in accordance with the invention.

The change to a catalyst with higher activity takes place generally after conversion of 30 to 95 mol %, preferably 50 to 90 mol %, in particular 60 to 90 mol %, of the alcohol to the alkyl mercaptan.

The catalysts used are in particular halogenated and halogen-free alkali metal tungstates or combinations of these compounds.

These are known, for example, from the applications WO 2005/021491, WO 2004/096760, WO 2006/015668 and PCT/EP/2005/012598.

In this case, preference is given to using catalysts comprising halogenated compounds, especially bromine compounds, in the 2nd section.

The halogenated catalysts used with preference in accordance with the invention generally have the formula $$A_xWO_YX_z$$

in which
A: at least one alkali metal, especially selected from the group of Na, K, Cs, Rb;
X: at least one halide selected from the group of F, Cl, Br, I,
x: 0.1 to 4, especially 1.2 to 3;
Y: this value is established according to the structure of the tungstate and the alkali metal content owing to the 6-valency of tungsten;
z: 0.01 to 12, in particular 0.9 to 4.

The size of z is a measure of the halide content in the tungstate, which need not be present in chemically bound form to the tungstate.

The halide constituent of the composition of the formula I consists of or comprises especially chloride when the tungstate comprises at least two different bound alkali metals and/or at least one further halide selected from the group of F, Br, I.

Chloride is preferably present alone as the halide when the molar ratio of Na or K/W in the catalyst is >0.9 to 1.9.

The alkali metal constituent of the catalytically active compound may be composed of one or more elements of the alkali metal group. The bound halogen constituent of the catalyst may likewise be composed of one or more different halides.

When the catalyst is present in the form of a supported catalyst, it contains the halogenated alkali metal tungstate in an amount of 8 to 50% by weight, in particular 15 to 40% by weight, preferably 20 to 36% by weight. In the case of a coated catalyst, these proportions are based on the composition of the coating.

The halogenated oxidic compounds composed of alkali metal(s) and tungsten may be impregnated directly onto a support body (supported catalyst).

In the preparation of catalysts in the form of extrudates or pellets, the pulverulent support is impregnated or mixed with the inventive oxidic composition, and the resulting intermediate is then shaped (unsupported catalyst). When a coated catalyst is prepared, the pulverulent support is impregnated with the catalytically active composition and the resulting mixture is then applied to a preferably inert support core in the form of a coating.

The molar halide/alkali metal ratio is more preferably 0.1:1 to 1:1. The inventive tungstates for the reaction of alkanols with hydrogen sulphide to give alkyl mercaptans, in contrast to the catalysts impregnated with caesium tungstate ($Cs_2WO_4$) or potassium tungstate ($K_2WO_4$) according to the prior art thus contain a proportion of halides.

It is found that the proportion of halides, especially on the aluminium oxide used with preference, in comparison to the non-halide-free alkali metal tungstate used exclusively in the prior art, imparts to the catalyst a significantly improved activity with simultaneously high selectivity. Moreover, as a result of the addition of halides to the alkali metal tungstate, it unexpectedly exhibits excellent selectivity at very high conversions of alcohol. According to the invention, an excellent conversion can be achieved at very high loadings with the promoter without the selectivity of the catalyst decreasing, as is known from the prior art for halide-free catalysts. It has also been found that the activity and selectivity of the catalyst can be adjusted in a controlled manner via the alkali metal-tungsten-halide ratio and via the selection of the alkali metals and of the halides. As a result of the possibility of using mixtures of compounds of different alkali metals or halogens, it is possible to replace comparatively expensive substances such as caesium, rubidium, bromine or iodine compounds at least partly with less expensive compounds, for example potassium or sodium compounds or chlorides, without the activity or selectivity of the catalyst being impaired.

The catalysts used in accordance with the invention are preferably used in the form of a supported catalyst in which the surface is impregnated with the catalytically active substance, or of a coated catalyst in which a preferably inert core is surrounded by a mixture of catalytically active substance and support material. In addition, extrudates or pellets in which the catalytically active substance is mixed with the pulverulent support material before shaping or the support material is impregnated with it may be used.

The support materials selected are the known oxidic inorganic compounds, for example $SiO_2$, $TiO_2$, $ZrO_2$ and preferably so-called active aluminium oxide.

This material has high specific surface areas between about 10 and 400 $m^2/g$ and consists mainly of oxides of the transition series of the crystallographic phases of aluminium oxide (see, for example, Ullmann's Encyclopedia of Industrial Chemistry of 1985, vol. Al, pages 561-562). These transition oxides include γ-, δ-, η-, κ-, χ- and θ-aluminium oxide. All of these crystallographic phases are converted to the thermally stable α-aluminium oxide when the aluminium oxide is heated to temperatures above 1100° C. Active aluminium oxide is supplied commercially in various qualities and supply forms for catalytic applications. For the preparation of supported catalysts, particularly suitable shaped bodies are those composed of granulated or extruded aluminium oxide with particle diameters of 1 to 5 mm, a specific surface area of 180 to 400 m²/g, a total pore volume between 0.3 and 1.2 ml/g and a bulk density of 300 to 900 g/l. For the purposes of the invention, preference is given to using aluminium oxide with a specific surface area of more than 200 m²/g, since the catalytic activity of the finished catalyst rises slightly with increasing surface area of the aluminium oxide. This material is preferably used in powder form for the preparation of the coated catalysts, extrudates or pellets.

The aqueous impregnation solution for the application of the promoter can be prepared in a simple manner from water-soluble alkali metal, tungsten and halogen compounds, especially tungstic acid ($H_2WO_4$), alkali metal hydroxides, optionally alkali metal halides or ammonium halides or hydrohalic acid. To this end, for example, tungstic acid is suspended in water and dissolved with addition of a base and heating. The desired alkali metal halide(s) or ammonium halides, optionally also the corresponding hydroxides and/or, for example, optionally a hydrohalic acid with the halide which may be desired are likewise dissolved in water and combined with the solution of the tungstic acid (promoter solution) so as to give rise to the desired composition ratios for the alkali metal tungstates and their halide content. As well as the alkali metal halides, it is also advantageously possible to use alkali metal salts whose anions can be driven out without residue by heat treatment, for example nitrates, formates, oxalates, acetates or carbonates. To stabilize the promoter solution having a pH of preferably 8 to 14, inorganic and also organic bases are used. Preference is given to using those which can be driven out without residue by a subsequent heat treatment of the catalyst obtained after the impregnation. These bases preferably include ammonium hydroxide and organic bases, especially amines.

This method neutralizes the acidic groups present on the surface of, for example, $Al_2O_3$ support materials to a large extent, generally at least 75%, in particular 100%.

The molar ratio of alkali metal compounds and halides in the aqueous impregnation solution is selected such that the new tungstates contain halides and alkali metals in a molar ratio of 0.01:1 to 3:1. In comparison to the known halide-free catalysts, this leads to a significantly increased yield in the case of use of the inventive catalysts, especially at low ratios of hydrogen sulphide and methanol in the reaction gas.

Preference is given to caesium tungstates, potassium tungstates and rubidium tungstates, especially caesium tungstates; halides are preferably fluoride, bromide and chloride, in particular fluoride and bromide.

Tungstates with different alkali metal cations or contents of different halides preferably contain cations of two different alkali metals and at least one halide, preferably in a ratio of halide to alkali metal between 0.01:1.0 and 3.0:1.0, where the molar proportions of alkali metals or any different halides present are counted as a sum. The proportion of the less expensive alkali metal or halide is increased to such an extent and, at the same time, that of the comparatively expensive alkali metal or halide is reduced in turn, such that no deterioration in the activity or selectivity of the catalyst occurs.

In the case of combinations of alkali metals, preference is given to tungstates in which the Cs or Rb content in the advantageous ratio is replaced by K or Na cations.

Preference is given to catalysts in which combinations deviating from a molar 1:1 ratio of bound alkali metals from the group of
potassium and caesium,
sodium and caesium,
rubidium and caesium,
sodium and potassium,
rubidium and potassium also occur.

In general, for the application of the promoter solution, various impregnation techniques, such as dipping impregnation, spray impregnation, vacuum impregnation and pore volume impregnation, may be used, and the impregnation can also be effected repeatedly. In the case of mouldings, the desired impregnation process must enable the application of the desired loading amount of the promoter with good evenness over the entire cross section.

Preference is given to applying the promoter solution to the shaped bodies in one or in two steps by spray or vacuum impregnation. In the spray impregnation, the aqueous impregnation solution is sprayed onto the support bodies. In the vacuum impregnation, a reduced pressure is generated in a vessel filled with the shaped bodies by means of a vacuum pump. Opening of a connection to the aqueous impregnation solution sucks the solution into the vessel until the entire bed of shaped bodies is covered with the solution. After an impregnation time of 0.2 to 2 hours, the solution which has not been taken up by the material is discharged or poured off.

Predrying for the period of 1 to 10 hours at room temperature allows the initial concentration gradient over the cross section of the shaped bodies to be largely balanced out. The uniformity of the impregnation is thus improved over the cross section of the catalyst particles. The catalyst precursors thus obtained are preferably dried at 100 to 200° C., preferably 100 to 140° C., for the period of 1 to 10 hours to remove the residual moisture. Then, a calcination is effected at 300 to 600° C., preferably 420 to 480° C., for the period of 1 to 20 hours, preferably 1 to 5 hours. This fixes the promoter on the aluminium oxide and decomposes and drives out the base of the impregnation solution. Optionally, the bed of the support bodies of the catalyst precursors can also be flowed through by a gas stream in the course of predrying, drying and calcination, which improves the transport of the residual moisture and of the decomposition gases away.

The impregnation of the shaped bodies can also be effected in more than one stage, especially two stages.

In this preferred embodiment, the solution used in the first stage then contains one to two thirds of the total amount of alkali metal and tungsten compounds envisaged.

When the procedure has several stages but at least two stages, the precursor obtained in the first stage is optionally not calcined.

Otherwise, in the second stage, the same impregnation, drying and calcination programme proceeds as described for the one-stage process.

This multistage impregnation is advisable in particular when high loadings are desired and/or the limited solubility of the promoter mixture do not enable loading in one step.

It is also possible to spray the support bodies or the support material repeatedly with the impregnation solution during the impregnation procedure and, between these treatment steps, in each case to remove parts of the residual moisture at a temperature of up to 120° C.

In the preparation of the coated catalyst, the powder to be applied to form a coating may be calcined before or after the coating. For example, this catalyst type can be prepared according to EP-B-0 068 193. In the case of preparation of extrudates or of pellets too, the calcination can also be effected before and/or after the shaping.

Apart from the chemical composition of the catalysts, the different activity in the reaction zones can also be achieved by altering the physical properties of the catalysts. It is known to those skilled in the art how the physical properties of a catalyst should be altered in order to increase or to lower the activity. Accordingly, in the different reaction zones, it is also possible to use catalysts with the same chemical composition but different specific surface area, size, shape (e.g. spheres, cylinders, hollow cylinders), pore radius distribution and/or different pore volume.

Different activities in the first and the following reaction chambers can also be obtained by diluting the amount of catalyst with inert materials (for example by means of pore-free shaped bodies such as glass spheres). In the subsequent reaction zones, the catalyst is then, in accordance with the invention, diluted with a smaller amount of inert material or used undiluted. The dilution is, for example, achieved by premixing the catalyst with the inert material (mechanical mixing), which is then filled into the reaction zone. The preferred volume ratio of catalyst to inert material is, according to the reaction zone, between 1:0 and 1:2. In the case of dilution of the amount of catalyst with inert material, preference is given to using the same catalyst in the different reaction zones.

This measure can also be combined with the above-described use of catalysts of different composition.

In a further embodiment of the invention, the reaction zones with different activity are not connected to one another directly but rather are disposed in separate apparatuses which are connected to one another via pipelines. This can be achieved, for example, through the series connection of reactors. The reactors may differ in design, size and flow control. A significant advantage in the case of division between different reactors is that the reaction conditions in the different reaction zones can be adjusted independently of one another in a simpler manner. Moreover, the catalysts can better be exchanged separately.

The inventive preferred process for preparing methyl mercaptans by reacting hydrogen sulphide and methanol over a catalyst is generally performed as a gas phase reaction in a tubular reactor. It is also possible to use a plurality of tubular reactors connected in series. In general, methanol and hydrogen sulphide are heated to a temperature which is high enough that both methanol and methyl mercaptan are present in the vapour phase but is below the decomposition temperature of methyl mercaptan. In general, the process according to the invention is performed at temperatures between 250 and 500° C., preferably between 300 and 450° C. The exact reaction temperature is dependent upon factors including the reaction pressure and the catalyst used.

The process according to the invention is performed generally at a pressure of 1 to 25 bar. It will be appreciated that the pressure is not selected at such a high level that the reactor feed or the methyl mercaptan condenses. The pressure in the process according to the invention is preferably 1 to 10 bar. For reasons of reduced emission risk, it can be adjusted to 1 to 3 bar, preferably to approximately ambient pressure.

The process according to the invention is generally performed continuously. The methyl mercaptan obtained is worked up by methods known to those skilled in the art.

The WHSV (weight hourly space velocity=weights of reactants/weight of catalyst per tube and hour) is generally 0.1 to 10 h$^{-1}$, preferably 0.1 to 5 h$^{-1}$, especially preferably 0.5 to 2 h$^{-1}$.

The process according to the invention has the advantage that the catalysts used need not be optimized with regard to all parameters. This is the case where only one catalyst type is used.

In that case, at the same time, the catalyst has to have a high activity, high selectivity for mercaptan formation and very low selectivities for the formation of parallel products from the reactant gases or by-products for the reaction of the mercaptans with one another. The problems which occur in that case always lead, unlike the process according to the invention, to losses in the mercaptan formation.

EXAMPLES

Comparative Example 1

In a heated tubular reactor with a reaction volume of 1.4 l, a reactant stream of 0.5 kg/h of methanol and 0.95 kg/h of hydrogen sulphide was fed in at a pressure of 9 bar. The reaction chamber was filled completely with a catalyst according to WO 2005/021491. At a wall temperature of 330° C. and a reaction temperature between 330 and 380° C. within the reaction chamber, a conversion of methanol of 90% was established at the reactor outlet. The selectivity for methyl mercaptan was 96%, the yield of methyl mercaptan 86.5%.

Comparative Example 2

In a heated tubular reactor with a reaction volume of 1.4 l, a reactant stream of 0.5 kg/h of methanol and 0.95 kg/h of hydrogen sulphide was fed in at a pressure of 9 bar. The reaction chamber was filled completely with a catalyst according to PCT/EP/2005/012898, and the halide content (Br) of the catalyst was 9.5% by weight. At a wall temperature of 320° C. and a reaction temperature between 320 and 370° C. within the reaction chamber, a conversion of methanol of 99% was established at the reactor outlet. The selectivity for methyl mercaptan was 93%, the yield of methyl mercaptan 92%.

Example

In a heated tubular reactor with a total reaction volume of 1.4 l, a reactant stream of 0.5 kg/h of methanol and 0.95 kg/h of hydrogen sulphide was fed in at a pressure of 9 bar. The reaction chamber was filled, in the first, upper reaction zone (60% of the total reaction volume), with the catalyst identical to that in Comparative Example 1. In the second, lower reaction zone (40% of the total reaction volume), the catalyst identical to that in Comparative Example 2 was disposed. At a wall temperature of 320° C., a reaction temperature between 320 and 380° C. within the first reaction zone and between 320 and 325° C. within the second reaction zone, a conversion of methanol of 99% was established at the reactor outlet. The selectivity for methyl mercaptan was 95.5%, the yield of methyl mercaptan 94.5%.

The invention claimed is:

1. A process for preparing alkyl mercaptans by a catalytic gas phase reaction of alkanols and hydrogen sulphide reactants over an alkali metal tungstate, said reactants being introduced in at least two successive reaction zones which contain different catalysts, such that an activity with respect to mercaptan formation of a first catalyst used in a first reaction zone is lower than an activity with respect to mercaptan formation of a second catalyst used in a second reaction zone or any subsequent reaction zones, and there is no feeding of the reactants between reaction zones.

2. Process according to claim 1, in which the catalyst in the second zone catalyses the conversion of the alkyl mercaptan formed to by-products only insignificantly, if at all.

3. Process according to claim 1, in which the catalyst in the first zone catalyses the reaction of alkanols and hydrogen sulphide to by-products only insignificantly, if at all.

4. Process according to claim 1, in which halogenated and/or halogen-free alkali metal tungstates are used as catalysts.

5. Process according to claim 1, in which a halide-free alkali metal tungstate is used in the first reaction zone and a halogenated alkali metal tungstate in the second reaction zone.

6. Process according to claim 5, characterized in that a brominated alkali metal tungstate is used.

7. Process according to claim 1, in which the change to a catalyst having a higher activity for mercaptan formation compared to that used in the first reaction zone is effected after the reaction of 30 to 95% of the alcohol used in the first reaction zone.

8. Process according to claim 2, in which the lower activity of the catalyst in the first reaction zone is achieved by the dilution of the amount of catalyst with solid inert material.

9. Process according to claim 8, in which the same catalyst is used in the first and the second or further reaction zone(s).

10. Process according to claim 2, in which the lower activity of the catalyst in the first reaction zone is achieved by the variation of one or more physical properties selected from the group of specific surface area, pore radius distribution, pore volume, pellet diameter and pellet shape.

11. Process according to claim 1, in which the reaction zones follow in succession in different reactors which are connected to one another in series.

12. Process according to claim 1, in which the reaction zones are connected to one another directly.

13. Process according to claim 1, in which hydrogen sulphide and methanol are reacted to give methyl mercaptan.

14. Process according to claim 1, in which the catalyst further comprises at least one halide selected from F, Cl, Br and I.

15. Process according to claim 14, in which the halide is provided only in the second reaction zone.

16. Process according to claim 14, in which the halide is Br.

17. Process according to claim 15, in which the halide is Br.

* * * * *